United States Patent [19]
Omata et al.

[11] Patent Number: 5,463,085
[45] Date of Patent: Oct. 31, 1995

[54] SYNTHESIS METHOD OF PHYSIOLOGICALLY ACTIVE DELTA-LACTONE

[75] Inventors: Tetsuo Omata; Kaichi Tanida, both of Osaka, Japan

[73] Assignee: Nitto Denko Corporation, Osaka, Japan

[21] Appl. No.: 257,523

[22] Filed: Jun. 9, 1994

[30] Foreign Application Priority Data

Jun. 10, 1993 [JP] Japan .................................. 5-166041

[51] Int. Cl.⁶ .................................................. C07D 309/30
[52] U.S. Cl. ............................................................. 549/273
[58] Field of Search ............................................... 549/273

[56] References Cited

U.S. PATENT DOCUMENTS 4,864,056  9/1989  Senda et al. ............................ 560/179

OTHER PUBLICATIONS

*R–3–Methyl–γ–butyrolactone as a Template for the Syntheses of (+)–Invictolide*, Ziegler et al, Tetrahedron Letters, vol. 27, No. 11, pp. 1229–1232, (1986).

*Isolation of the Trail Recruitment Pheromone of Solenopsis invicta*, Meer et al, Journal of Chemical Ecology, vol. 14, No. 3, pp. 825–838, (1988).

*Synthesis of Homofarnesenes: Trail Pheromone Components of the Fire Ant, Solenopsis Invicta*, Alvarez et al, Tetrahedron, vol. 43, No. 13, pp. 2897–2900, (1987).

*Synthesis of (–)–Invictolide, the Peromone Component of the Red Imported Fire Ant*, Senda et al, Agric. Biol. Chem., 51(5), pp. 1379–1384, (1987).

*Synthesis and Stereochemistry of Tetrahydro–3, 5–Dimethyl–6–(1–Methylbutyl)–2H–Pyran–2–One, etc.*, Rocca et al, Tetrahedron Letters, vol. 24, No. 18, pp. 1893–1896, (1983).

Primary Examiner—C. Warren Ivy
Assistant Examiner—Ba K. Trinh
Attorney, Agent, or Firm—Sughrue, Mion, Zinn, Macpeak & Seas

[57] ABSTRACT

A synthesis method of physiologically active δ-lactone, which comprises addition-reacting diethyl methylmalonate and methacrolein in the presence of a base.

12 Claims, 2 Drawing Sheets

SYNTHESIS METHOD OF PHYSIOLOGICALLY ACTIVE DELTA-LACTONE

FIELD OF THE INVENTION

The present invention relates to a synthesis method of a physiologically active lactone. More particularly, it relates to a synthesis method of a physiologically active δ-lactone capable of synthesizing one component of the queen recognition pheromone of the red imported fire ant (*Solenopsis invicta*) simply in a short step at a high optical purity and which can be widely used as an industrial synthesis method.

BACKGROUND OF THE INVENTION

The red imported fire ant (*Solenopsis invicta*) is an injurious insect giving great damages to agricultural products such as soybean, etc., through middle South America to the southern and middle part of the United States of America. A method of using chlorine series agricultural chemicals such as dieldrin, etc., had conventionally been used as a method of controlling the red imported fire ant (*Solenopsis invicta*), but from the problems of a chronic toxicity, an in-soil remaining property, etc., the use of the chlorine series agricultural chemicals have been entirely prohibited.

With the prohibition of using the agricultural chemicals, various controlling methods have been investigated and, in particular, a method of using a pheromone and an anticidal agent has recently been noticed in the United States of America [*Tetrahedron*, 43(13), 2897–2900(1987), and *J. Chem. Ecol.*, 14(3), 825–838(1988)].

Further, of the pheromones of the red imported fire ant (*Solenopsis invicta*), the queen recognition pheromone is a pheromone with which working ants recognize the queen ant and it is reported that ants can be effectively controlled by utilizing the queen recognition pheromone.

Three kinds of components represented by the following formulae (I), (II), and (III) are known as the queen recognition pheromone of the red imported fire ant (*Solenopsis invicta*). Of those components, (−)-3,5-dimethyl-6-(1′-methylbutyl)-2H-tetrahydropyran-2-one represented by the formula (II) called invictolide has 4 asymmetric carbon atoms in the structural molecule, and the synthesis of the compound is very difficult.

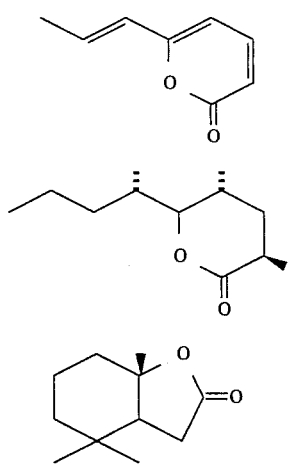

A stereoselective synthesis method of (−)-3,5-dimethyl-6-(1′-methylbutyl)-2H-tetrahydropyran-2-one (invictolide) described above is shown in the report by Ziegler et al [*Tetrahedron Letters*, 27, 1229(1989)]. However, this method has the problems that the method includes very many reaction steps, and the optical purity of invictolide obtained is low, and hence this method is not a production method which can be widely used in an industrial purpose.

Under such circumstances, a synthesis technique capable of easily conducting the synthesis of invictolide is disclosed in U.S. Pat. No. 4,864,056.

The disclosed technique is a technique of synthesizing invictolide which is one component of the queen recognition pheromone, using an optically active hydroxy ester represented by the following formula (IV), and this technique can synthesize invictolide represented by the formula (II) at a high purity and with short steps as compared with the above-described method reported by Ziegler et al.

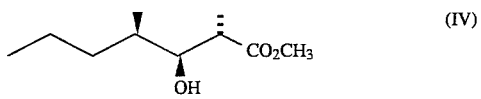

However, the stereoselective synthesis method of invictolide using the hydroxy ester disclosed in U.S. Pat. No. 4,864,056 described above involves the problems that 13 reaction steps described hereinafter must be passed from the synthesis of the optically active hydroxy ester to the synthesis of invictolide and hence the synthesis method is not a sufficient technique as a synthesis method which is widely used as an industrial method.

The synthesis steps shown in the techniques already disclosed are explained by the reaction schemes 1 to 3 shown below.

First, an optically active epoxide (b) is synthesized from an optically active amino acid (a) as shown in following reaction scheme 1.

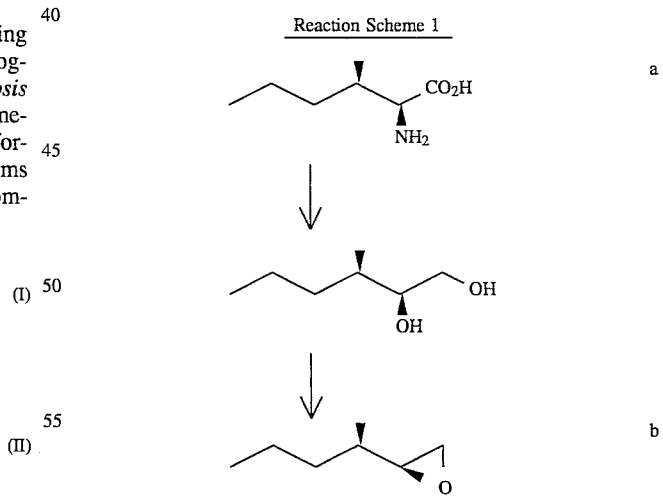

Next, the epoxide (b) is subjected to a ring-opening reaction and an acid treatment according to the following reaction scheme 2 to obtain a hydroxylic acid (c) and the hydroxylic acid (c) is methyl-esterified to obtain a hydroxy ester (d). Furthermore, the hydroxy ester (d) is reacted with lithium diisopropylamide and methyl iodide in the presence of a base to α-methylate the ester and is then through a separation and purification step to synthesize an optically active hydroxy ester (e).

Reaction Scheme 2

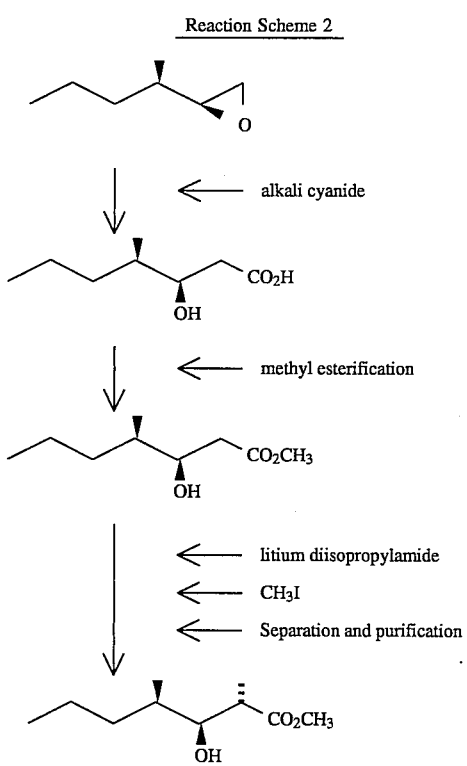

Using the optically active hydroxy ester (e) thus synthesized, invictolide (k) is synthesized according to the reaction scheme 3 shown below.

First, the optically active hydroxy ester (e) is reacted with dihydropyran in the presence of an acid catalyst to synthesize a compound (f) the hydroxy group of which is protected, and the product obtained is then reduced with aluminum lithium hydride to obtain a compound (g). The compound (g) is tosylated to obtain a compound (h), the compound (h) is iodinated to synthesize a compound (i), and the compound (i) is then asymmetrically alkylated to obtain a compound (j). The compound (j) is subjected to an acid treatment to obtain the invictolide (k).

Reaction Scheme 3

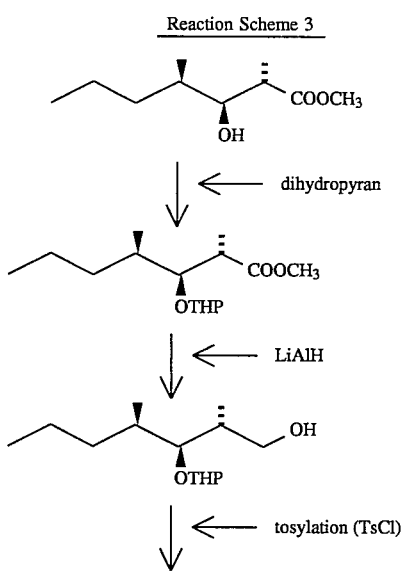

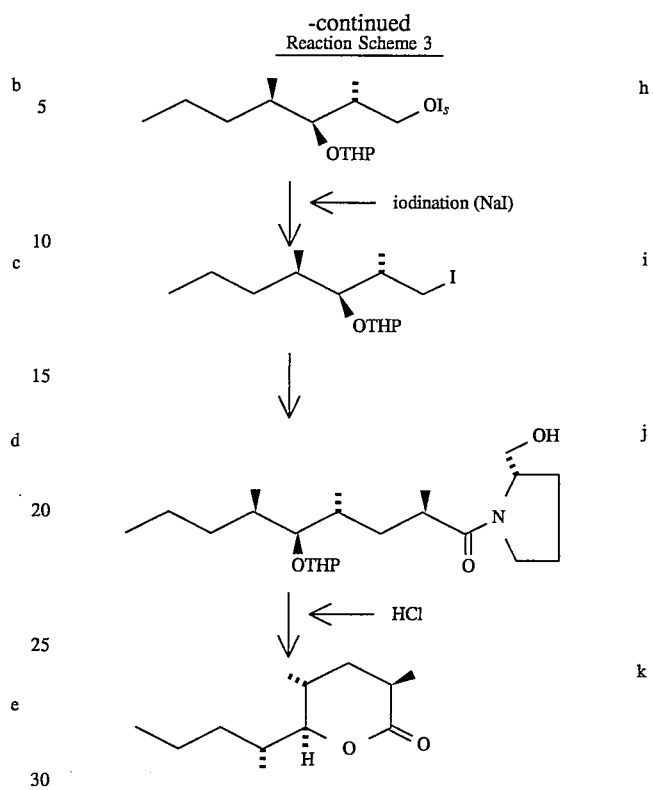

As described above, many reaction steps are also required in the synthesis technique already disclosed and hence the synthesis technique is not a sufficient technique which is widely used as an industrial synthesis method.

Thus, the development of an excellent synthesis method capable of synthesizing invictolide, which is a component of the gueen recognition pheromone, at a high optical purity and easily in less reaction steps and capable of establishing as an industrial production method has been desired in the field of the art.

SUMMARY OF THE INVENTION

Accordingly, an object of the present invention is to provide a synthesis method of a physiologically active δ-lactone, which can overcome the problems involved in the conventional synthesis technique.

The synthesis method of physiologically active δ-lactone according to the present invention comprises addition-reacting diethyl methylmalonate and methacrolein in the presence of a base.

According to the synthesis method of the present invention, invictolide [3,5-dimethyl-6-(1'-methylbutyl)-2 H-tetrahydropyran-2-one] wherein 4 asymmetric carbon atoms are not optically controlled, represented by the following formula (V) can be easily synthesized by only using a less number of steps and hence the synthesis method of the present invention can be widely used as an industrial synthesis method.

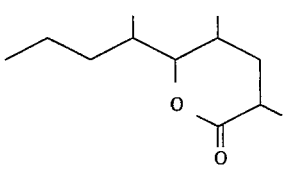

Further, the invictolide, which is not optically controlled, synthesized by the synthesis method of the present invention can be easily converted by an optical resolution method, into one component of the queen recognition pheromone of the red imported fire ant (*Solenopsis invicta*), that is, the invictolide [(−)-3,5-dimethyl-6-(1'-methylbutyl)-2 H-tetrahydropyran-2-one] represented by the formula (II).

Furthermore, even the invictolide [3,5-dimethyl-6-(1'-methylbutyl)-2H-tetrahydropyran-2-one] which is not optically controlled can be expected to function as the queen recognition pheromone, i.e., the invictolide [(−)-3,5-dimethyl-6-(1'-methylbutyl)-2H-tetrahydropyran-2-one].

DETAILED DESCRIPTION OF THE INVENTION

Figure 1:
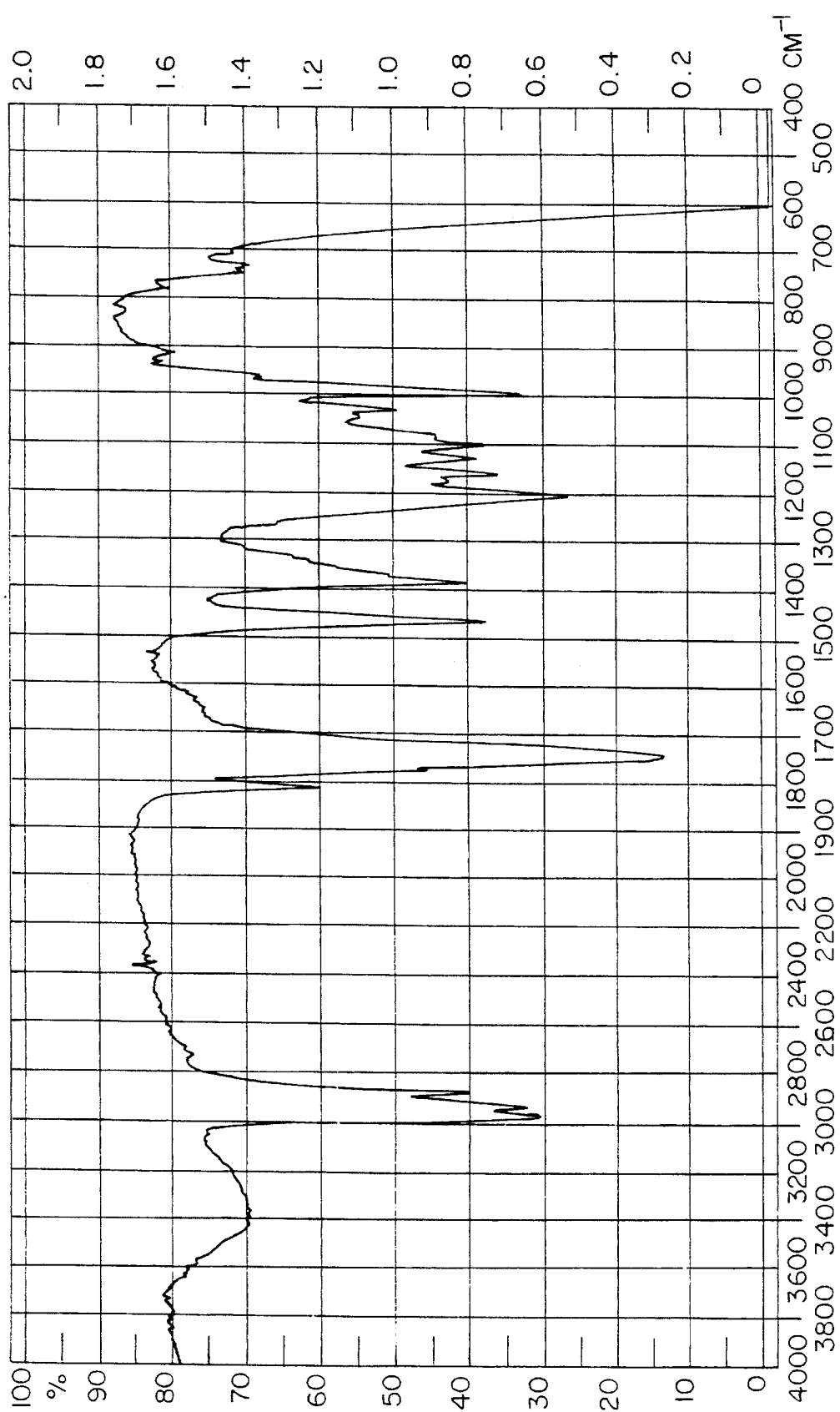
FIG. 1 is a chart showing the infrared absorption spectra (IR) of (−)-3,5-dimethyl-6-(1'-methylbutyl)-2 H-tetrahydropyran-2-one obtained by the synthesis method of physiologically active δ-lactone of the present invention.

The synthesis method of physiologically active δ-lactone of the present invention is explained in detail below.

As shown in the following reaction scheme 4, diethyl methylmalonate (1) and methacrolein (2) are used as the starting materials, and those raw materials are condensed in a solvent in the presence of a base (3) to synthesize an intermediate, 4,4-diethoxycarbonyl-2-methylpentanal (4).

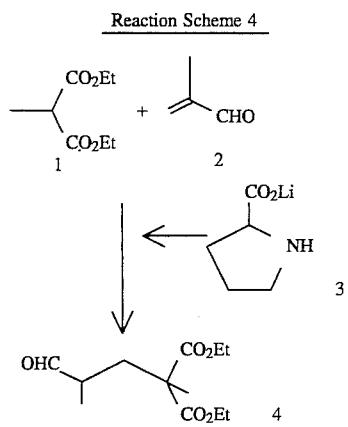

Reaction Scheme 4

In the reaction step, it is preferred to use diethyl methylmalonate such that the amount of diethyl methylmalonate is from about 1 to 5 parts by weight per 1 part by weight of methacrolein.

The reason for this is that if the amount of diethyl methylmalonate used is less than 1 part by weight per 1 part by weight of methacrolein, it becomes difficult to obtain the desired synthetic intermediate at a high yield, and on the other hand, if the amount thereof is over 5 parts by weight, the removal of the excessive portion is required, which is economically disadvantageous.

Further, the base used in the reaction step is preferably L-proline lithium salt.

The reason for this is based on the inventors' experimental knowledge that when diethyl methylmalonate is reacted with methacrolein in the presence of L-proline lithium salt, reaction proceeds under a very mild temperature condition of from 20° to 40° C. and the synthetic intermediate, 4,4-diethoxycarbonyl-2-methylpentanal (4) can be synthesized at a high yield of at least about 70%.

It is generally known that diethyl malonate is reacted with each of various α,β-unsaturated carbonyl compounds in the presence of a base, that is, a so-called Michael addition reaction proceeds.

However, if methyl group is present at the α-position of malonic acid, it is estimated that the reaction does not proceed or even if the reaction proceeds, the yield is greatly decreased, due to the steric hindrance and a lowering of the acidity of a-positioned acidic protone. In fact, when the inventors tried to use various bases such as sodium ethylate, sodium hydride, a ternary amine, etc., in order to proceed the reaction, 4,4-diethoxycarbonyl-2-methylpentanal was not obtained at all.

On the other hand, when L-proline lithium salt was present, 4,4-diethoxycarbonyl-2-methylpentanal could be synthesized at a high yield.

In the reaction step of the present invention, L-proline lithium salt is used in an amount of ⅕ to ¹⁄₂₀ equivalent.

The reason for this is that if the amount of L-proline lithium salt used is less than ¹⁄₂₀ equivalent, the synthetic intermediate, 4,4-diethoxycarbonyl-2-methylpentanal cannot synthesized at a high yield, while even if the amount thereof is over ⅕ equivalent, the reaction yield and the reaction rate are not further increased.

Any solvent capable of dissolving diethyl methylmalonate, methacrolein, and L-proline lithium salt, such as lower alcohols (e.g., methanol and ethanol) can be used without any particular restriction as a solvent used in the reaction.

The reaction is conducted at a temperature of from 20° to 40° C. for from about 2 to 7 hours.

4,4-Diethoxycarbonyl-2-methylpentanal thus obtained is reacted with a Grignard reagent and through a hydrolysis reaction, a neutralization reaction, and a decarboxylation reaction, the product is ring-closed into δ-lactone, whereby physiologically active δ-lactone which is the final product in the present invention is obtained.

The reaction steps are explained based on the reaction scheme 5.

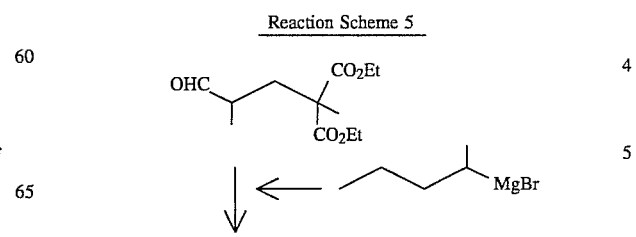

Reaction Scheme 5

-continued
Reaction Scheme 5

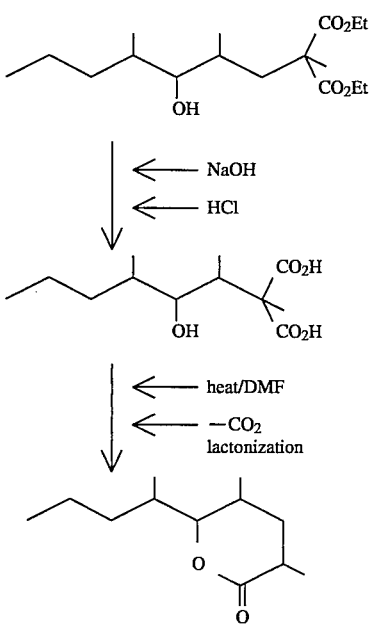

The synthetic intermediate, 4,4-diethoxycarbonyl-2-methylpentanal (4), obtained in the reaction step described above is reacted with a Grignard reagent (5) in a solvent. The reaction is conducted at a temperature of from about −30° C. to −10° C. for from about 5 to 8 hours.

There is no particular restriction on the Grignard reagent used, but sec-amyl magnesium bromide is preferably used as the Grignard reagent, since invictolide which is not optically controlled and is the object of the present invention can be synthesized in 4 steps on the whole.

There is also no particular restriction on the amount of the Grignard reagent used but the amount of the Grignard reagent used is preferably from about 1 to 1.5 equivalents in order to smoothly conduct the reaction.

Any solvent which does not hinder the reaction by the Grignard reagent can be used as the solvent, but ethers such as tetrahydrofuran, dioxane, etc., are practically preferably used.

A diethoxycarbonyl compound (6) is synthesized from the 4,4-diethoxycarbonyl-2-methylpentanal (4) by the reaction with the Grignard reagent.

The diethoxycarbonyl compound (6) thus obtained is hydrolyzed with an alkali and is then neutralized to obtain a dicarboxylic acid derivative (7).

The dicarboxylic acid derivative (7) obtained is heated in a high-boiling solvent such as nonprotonic polar solvents, e.g., dimethylformamide and dimethylacetamide, to be subjected to a decarboxylation treatment and at the same time to be ring-closed into δ-lactone to obtain invictolide wherein 4 asymmetrical carbon atoms are not optically controlled, i.e., 3,5-dimethyl-6-(1'-methylbutyl)-2H-tetrahydropyran-2-one (8), which is the final product of the present invention.

As described above, the present invention is a synthesis method, wherein diethyl methylmalonate and methacrolein are used as the starting materials, first; the synthetic intermediate, 4,4'-diethoxycarbonyl-2-methylpentanal represented by the following formula (VI) is synthesized using the raw materials; the intermediate is reacted with a Grignard reagent to form a diethoxycarbonyl compound represented by the following formula (VII), and after forming a dicarboxylic acid derivative represented by following formula (VIII) from the diethoxycarbonyl compound through an alkali hydrolysis and a neutralization reaction, the dicarboxylic acid derivative is lactonized to obtain the invictolide wherein 4 asymmetric carbon atoms are not optically controlled, that is, 3,5-dimethyl-6-(1'-methylbutyl)-2H-tetrahydropyran-2-one represented by the formula (V). Therefore, the synthesis method of the present invention is a synthesis method capable of obtaining the final product by very less steps and having a high utilization value as an industrial production method.

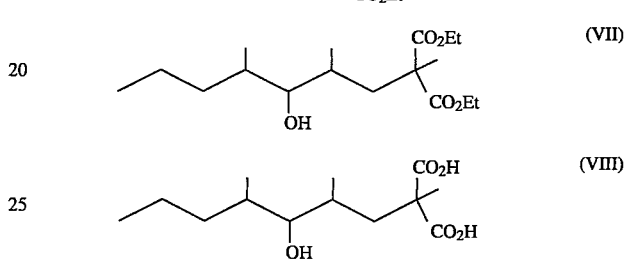

Further, 3,5-dimethyl-6-(1'-methylbutyl)-2 H-tetrahydropyran-2-one obtained above can function, as it is, the same action as the invictolide, [(−)-3,5-dimethyl-6-(1' -methylbutyl)-2H-tetrahydropyran-2-one], which is one component of the queen recognition pheromone of the red imported fire ant (*Solenopsis invicta*).

Furthermore, after clathrating 3,5-dimethyl-6-(1' -methylbutyl)-2H-tetrahydropyran-2-one obtained with cholic acid or a derivative thereof to obtain a clathrate compound, a guest compound which is easily guest-exchanged with 3,5-dimethyl-6-(1'-methylbutyl)-2H-tetrahydropyran-2-one is dissolved in the clathrate compound, and by isolating the clathrated guest compound, the product can be easily purified into the invictolide, [(−)-3,5-dimethyl-6-(1'-methylbutyl)-2 H-tetrahydropyran-2-one] which is one component of the queen recognition pheromone of the red imported fire ant (*Solenopsis invicta*).

As described above in detail, since the present invention is a synthesis method of physiologically active δ-lactone, which comprises addition-reacting diethyl methylmalonate and methacrolein in the presence of a base, the queen recognition pheromone capable of being effectively used for controlling the red imported fire ant (*Solenopsis invicta*) which gives great damages onto agricultural products can be synthesized in far short steps as compared with conventional synthesis techniques and easily at a high optical purity, whereby the synthesis method of the present invention has an excellent effect that the method can be widely used as an industrial synthesis technique.

The effects of the synthesis method of physiologically active δ-lactone of the present invention are more clarified by the following examples. However, the following examples do not limit the present invention in any way.

EXAMPLE 1

After dissolving 250 g (1.44 mols) of diethyl methylmalonate and 17.5 g (0.144 mol) of L-proline lithium salt in 800 ml of methanol, 300 ml of a methanol solution having dissolved therein 110 g (1.57 mols) of methacrolein was added dropwise to the solution over a period of 2 hours while maintaining the temperature at 20°–30° C.

After completion of the addition, the mixture was stirred at a temperature of from 30° to 50° C. for 5 hours and after confirming the consumption of diethyl methylmalonate of the raw material by a thin-layer chromatography, the reaction mixture was neutralized with acetic acid.

After concentrating and distilling off methanol to a half thereof under reduced pressure, water was added to the residue to extract with toluene. The toluene solution obtained was washed with water, concentrated under reduced pressure, and distilled (boiling point: 113° to 117° C. at 3 mmHg) to obtain 245 g (yield 69.4%) of the desired product, 4,4-diethoxycarbonyl-2-methyl-1-pentanal having a chemical purity of 95% (by Gas Chromatography).

EXAMPLE 2

According to the conventional method, 700 ml of a tetrahydrofuran solution of a Grignard reagent was prepared from 151 g (1.0 mol) of (±)-2-bromopentane and 24 g of magnesium.

Apart from this, 240 g (0.98 mol) of 4,4-diethoxycarbonyl-2-methyl-1-pentanal obtained in Example 1 was dissolved in 500 ml of tetrahydrofuran and while stirring the solution at −30° C., the tetrahydrofuran solution of the Grignard solution prepared above was added dropwise to the solution over 2 hours. After completion of the addition, the temperature of the mixed solution was raised to a temperature of from −15° C. to −10° C. and the solution was stirred at this temperature for 3 hours. After completion of the reaction, the reaction mixture was treated with hydrochloric acid/ice-water mixture and after extracting the product with toluene, the toluene solution was dried and concentrated under reduced pressure to obtain 248 g (rough yield 78%) of a residual oily product. The residual oily product was supplied to the subsequent reaction without purification.

EXAMPLE 3

After dissolving 248 g (0.78 mol) of the residual oily material obtained in Example 2 in 400 ml of methanol, the hydrolysis reaction was conducted with 620 ml of a 3N sodium hydroxide aqueous solution. That is, the mixed solution was refluxed with stirring at a reaction temperature of 80° C. for 3 hours. After completion of the reaction, insoluble matters were removed by separating the liquid (aqueous solution) at hot state. The aqueous solution obtained was cooled to room temperature, and extracted twice each time with 600 ml of a mixture of tetrahydrofuran and ethyl acetate (v/v=1/1) acidified with 650 ml of 3N hydrochloric acid. The extract was washed with a saturated aqueous sodium chloride solution, and dried, and the solvent was distilled off under reduced pressure to obtain 135 g (rough yield 66.6%) of a residual oily product. The oily product was supplied to the subsequent reaction without purification.

EXAMPLE 4

After dissolving 135 g (0.52 mol) of the oily product obtained in Example 3 in 150 ml of dimethylformamide, the solution was refluxed with stirring. Generation of carbon dioxide was observed at an inside temperature of from 80° to 90° C.

The temperature of the solution was raised to a temperature of from 150° to 155° C. as it was and the reaction was conducted for 1 hour with stirring. The reaction mixture obtained was cooled to 30° C. and after adding thereto a large and sufficient amount of water, the product formed was extracted twice with toluene. The toluene layers obtained were combined, washed, dried, and concentrated under reduced pressure to obtain a residual oil. The residual oil was distilled (boiling point: 113° to 114° C. at 3 mmHg) to obtain 45 g (yield 43.7%) of the final product, 3,5-dimethyl-6-(1'-methylbutyl)-2H-tetrahydropyran-2-one.

EXAMPLE 5

In 200 ml of hexane was dissolved 40 g (0.20 mol) of 3,5-dimethyl-6-(1'-methylbutyl)-2H-tetrahydropyran-2-one obtained in Example 4, and after dissolving 5.1 g (0.013 mol) of cholic acid recrystallized from methanol in the solution thus obtained, the resulting mixture was allowed to stand overnight. Crystals thus formed were collected by filtration, washed with a small amount of ether, and air-dried to obtain 7.5 g (0.012 mol) of a clathrate compound at a yield of 95%.

The clathrate compound was immersed in 50 ml of acetonitrile at room temperature for 10 minutes to exchange the guest compound of the clathrate molecule with acetonitrile. Crystals formed were filtered off and the filtrate obtained was concentrated to obtain 2.1 g (0.011 mol) of the invictolide, [(−)-3,5-dimethyl-6-(1'-methylbutyl)-2H-tetrahydropyran-2-one] (optical yield 84%).

Figure 2:
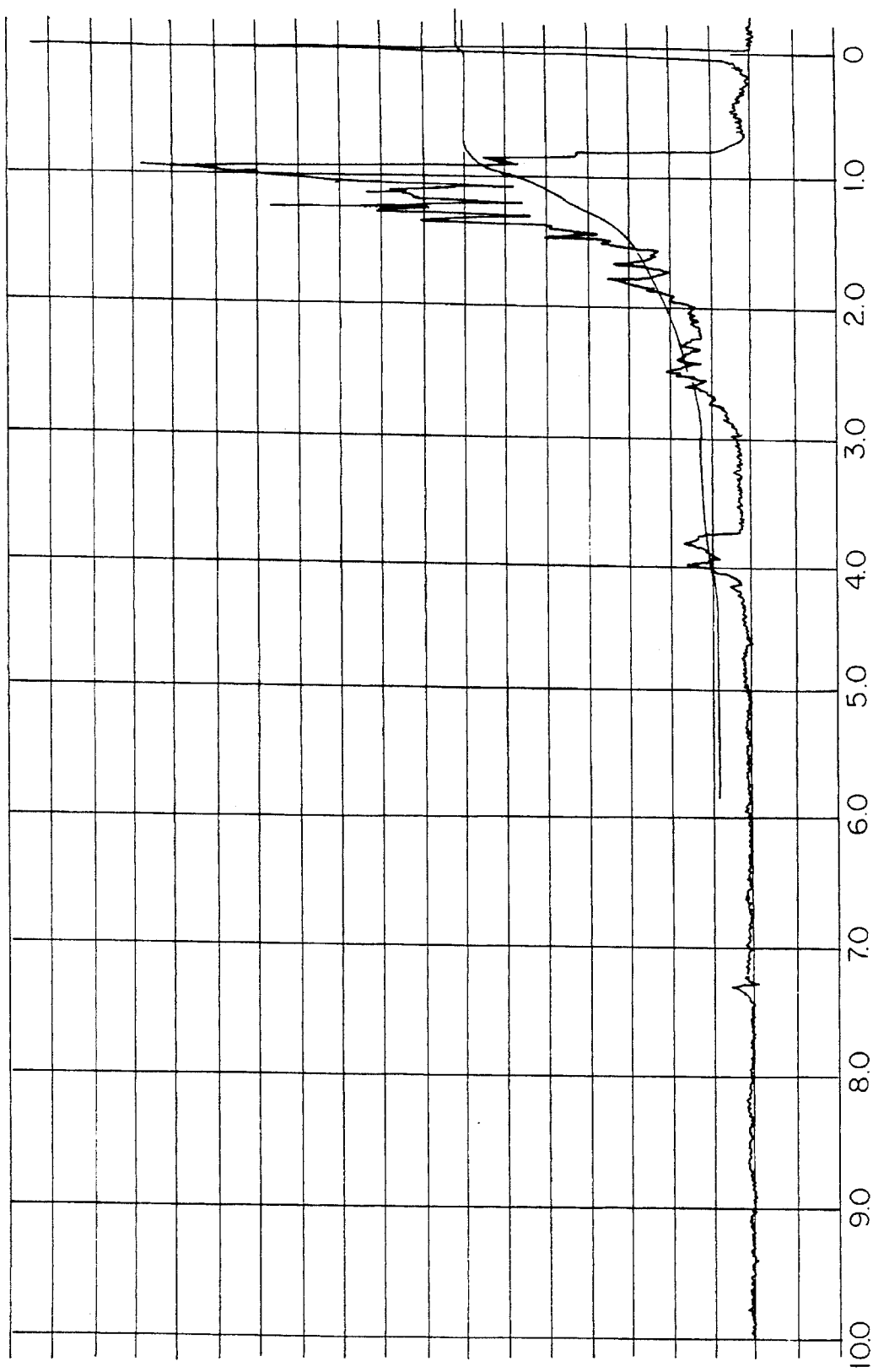
FIG. 2 is a chart showing a proton magnetic resonance specra (NMR) of (−)-3,5-dimethyl-6-(1'-methylbutyl)-2 H-tetrahydropyran-2-one obtained by the synthesis method of physiologically active δ-lactone of the present invention.

The strucrue of (−)-3,5-dimethyl-(1'-methylbutyl)-2 H-tetrahydropyran-2-one obtained was identified by that the specific rotation $[\alpha]_D^{20}$ was −105° (c=0.3, chloroform); the absorption wavenumbers (1∨ max cm$^{-1}$) of the infrared absorption spectra (IR) were 2960 (s), 2930 (s), 2870 (m), 1740 (s), 1460 (m), 1380 (m), 1330 (w), 1235 (m), 1195 (s), 1150 (m), 1120 (m), 1090 (m), 1020 (m), 990 (m), and 720 (w) (as shown in FIG. 1); and the σ values of the proton magnetic resonance spectra [NMR, δ(CDCl$_3$)] were 0.90 (3H, t, J=7.5 Hz), 1.25 to 1.51 (4H, m), 1.65 to 1.74 (3H, m), 1.85 to 2.05 (1H, m), 2.58 to 2.70 (1H, m), and 3.90 (1H, dd, J=2, 10 Hz) (as shown in FIG. 2).

While the invention has been described in detail and with reference to specific embodiments thereof, it will be apparent to one skilled in the art that various changes and modifications can be made therein without departing from the spirit and scope thereof.

What is claimed is:

1. A synthesis method of physiologically active δ-lactone, which comprises addition-reacting diethyl methylmalonate and methacrolein in the presence of a base, wherein the base is L-proline lithium salt.

2. A synthesis method as claimed in claim 1, wherein the dimethyl methylmalonate is used in an amount of from 1 to 5 parts by weight per 1 part by weight of the methacrolein.

3. A synthesis method as claimed in claim 1, wherein the L-proline lithium salt is used in an amount of from ⅕ to 1/20 equivalent.

4. A synthesis method as claimed in claim 1, wherein the addition reaction is conducted at a temperature of from 20° to 40° C. for from about 2 to 7 hours.

5. A synthesis method as claimed in claim 1, wherein the addition reaction is conducted in a solvent.

6. A synthesis method as claimed in claim 5, wherein the solvent is a lower alcohol.

7. A synthesis method as claimed in claim 1, wherein 4,4-diethoxycarbonyl-2-methylpentanal is obtained by the addition reaction, and the 4,4-diethoxycarbonyl-2-methylpentanal is reacted with a Grignard reagent in a solvent.

8. A synthesis method as claimed in claim 7, wherein the Grignard reagent is used in an amount of from about 1 to 1.5 equivalents.

9. A synthesis method as claimed in claim 7, wherein the Grignard reagent is sec-amyl magnesium bromide.

10. A synthesis method as claimed in claim 7, wherein the solvent is ethers.

11. A synthesis method as claimed in claim 7, wherein the reaction with a Grignard reagent is conducted at a temperature of from about −30° to −10° C. for from about 5 to 8 hours.

12. A synthesis method as claimed in claim 1, wherein the physiologically active δ-lactone is 3,5-dimethyl-6-(1'-methylbutyl)-2H-tetrahydropyran-2-one represented by the following formula (V)

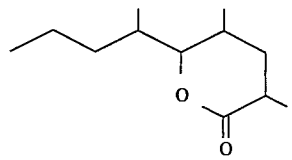

* * * * *